(12) United States Patent
Dominguez et al.

(10) Patent No.: US 6,893,447 B2
(45) Date of Patent: May 17, 2005

(54) SURGICAL REFERENCE FRAME FIXATION DEVICE WITH CANNULATED POST AND METHOD OF USE

(75) Inventors: Leonel Dominguez, Jacksonville, FL (US); Michael S. Ferrell, Orange Park, FL (US); Prasad Nalluri, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 546 days.

(21) Appl. No.: 09/961,616

(22) Filed: Sep. 24, 2001

(65) Prior Publication Data

US 2002/0038126 A1 Mar. 28, 2002

Related U.S. Application Data

(60) Provisional application No. 60/235,216, filed on Sep. 24, 2000.

(51) Int. Cl.[7] .............................................. A61B 19/00
(52) U.S. Cl. ........................... 606/130; 606/54; 606/96; 600/417
(58) Field of Search ............................. 606/130, 54–59, 606/86, 96–98; 600/414–417, 421, 424

(56) References Cited

U.S. PATENT DOCUMENTS

| | | |
|---|---|---|
| 5,254,079 A | 10/1993 | Agboedoe et al. |
| 5,300,076 A | 4/1994 | Leriche |
| 5,387,220 A | 2/1995 | Pisharodi |
| 5,388,580 A | 2/1995 | Sullivan et al. |
| 5,591,175 A | 1/1997 | Juto |
| 5,601,569 A | 2/1997 | Pisharodi |
| 5,618,288 A | 4/1997 | Calvo |
| 5,643,268 A | 7/1997 | Vilsmeier et al. |
| 5,649,936 A | 7/1997 | Real |
| 5,662,111 A | 9/1997 | Cosman |
| 5,695,501 A | 12/1997 | Carol et al. |
| 5,752,962 A | 5/1998 | D'Urso |
| 5,769,789 A | 6/1998 | Wang et al. |
| 5,775,337 A | 7/1998 | Hauger et al. |
| 5,776,143 A | 7/1998 | Adams |
| 5,797,924 A | 8/1998 | Schulte et al. |
| 5,799,099 A | 8/1998 | Wang et al. |
| 5,800,352 A | 9/1998 | Ferre et al. |
| 5,817,106 A | 10/1998 | Real |
| 5,829,444 A | 11/1998 | Ferre et al. |
| 5,855,582 A | 1/1999 | Gildenberg |
| 5,891,034 A | 4/1999 | Bucholz |
| 5,916,164 A | 6/1999 | Fitzpatrick et al. |
| 5,954,647 A | 9/1999 | Bova et al. |
| 5,967,980 A | 10/1999 | Ferre et al. |
| 5,971,997 A | 10/1999 | Guthrie et al. |
| 5,993,463 A | 11/1999 | Truwit |

(Continued)

*Primary Examiner*—(Jackie) Tan-Uyen T. Ho
(74) *Attorney, Agent, or Firm*—Trevor D. Arnold; Timothy A. Czaja

(57) ABSTRACT

A surgical fixation device for mounting a stereotactic reference frame to a patient. The device includes a mounting bracket assembly, a cannulated post, a base, an anchor tube, a plurality of percutaneous pins, and a driving device. The mounting bracket assembly is connected to a top portion of the post, whereas the base is slidably coupled to a bottom portion of the post, and defines a plurality of legs. The anchor tube extends distally from the post. The percutaneous pins extend distally from the legs, respectively. Finally, the driving device is connected to the post and is adapted to selectively contact the base. Upon final assembly, the base is longitudinally moveable relative to the anchor tube. The base can be moved to a retracted position such that the anchor tube is readily securable to a bony structure of the patient's anatomy. Once secured, the base can be moved distally such that the percutaneous pins engage the bony structure as well, thereby promoting overall stability of the device.

55 Claims, 5 Drawing Sheets

U.S. PATENT DOCUMENTS

| | | |
|---|---|---|
| 6,006,126 A | 12/1999 | Cosman |
| 6,011,987 A | 1/2000 | Barnett |
| 6,052,477 A | 4/2000 | Wang et al. |
| 6,071,288 A | 6/2000 | Carol et al. |
| 6,073,044 A | 6/2000 | Fitzpatrick et al. |
| 6,076,008 A | 6/2000 | Bucholz |
| 6,080,164 A | 6/2000 | Oshio et al. |
| 6,096,048 A | 8/2000 | Howard, III et al. |
| 6,132,437 A | 10/2000 | Omurtag et al. |
| 6,491,699 B1 * | 12/2002 | Henderson et al. ......... 606/130 |
| 6,595,999 B2 * | 7/2003 | Marchione et al. ........... 606/96 |

* cited by examiner

SURGICAL REFERENCE FRAME FIXATION DEVICE WITH CANNULATED POST AND METHOD OF USE

CROSS-REFERENCE TO RELATED APPLICATIONS

This application claims the benefit of, and incorporates herein by reference an entirety of, U.S. Provisional Application Ser. No. 60/235,216, filed on Sep. 24, 2000.

BACKGROUND OF THE INVENTION

The present invention relates to a bone fixation device for use in maintaining a surgical reference frame. More particularly, it relates to a minimally invasive bone post apparatus for maintaining a dynamic reference frame relative to a patient as part of a stereotactic system, and related method of use.

Stereotactic surgical systems provide surgeons with visual guidance information relating to surgical instruments/probes relative to an enclosed anatomical position, especially within the head or cranium. Basically, a stereotactic surgical system provides a quantitative determination of an anatomical position based upon a scanned image, such as a CAT scan, MRI scan, PET scan, etc. The scanned information is processed by a computer to produce a displayable image of the head. Subsequently, during a surgical procedure, the stereotactic system relates a position of a surgical instrument otherwise deployed within the anatomical body of interest (e.g., the head) relative to the previously-generated scanned information in visual form.

Stereotactic devices are highly useful in the field of neurosurgery as well as other fields, and more recently ENT procedures requiring instrument deployment in close proximity to the optic nerve, carotid artery, skull base, facial nerve, internal auditory canal, etc. A more recent stereotactic system is optical or camera based in which two cameras are employed to visualize a surgical field, digitize the viewed information from the cameras, and relate it via computer graphics to image data generated by the above-described image scanning techniques. The relationship of the optical cameras view and the image data will then make quantitative the anatomy seen in the camera view and also make quantitative the position of surgical instruments such as probes, microscopes, or space pointers, etc. relative to the anatomy via registration of the camera view to the image data. An example such a tandem optical, stereotactic device is available under the trade name LandmarX™ ENT Image Guidance System, from Medtronic-Xomed of Jacksonville, Fla.

Regardless of the exact stereotactic system configuration, a stereotactic or dynamic reference frame must be fixed to the patient's anatomy to provide accurate positioning information. For example, with surgical procedures at or near the patient's head, the reference frame must be affixed to the patient's head via an auxiliary device. To this end, skull posts are commonly employed to rigidly affix the reference frame to the cranium. In general terms, available skull post designs employ one or more bone screws embedded through a relatively large incision into the cranium. In this regard, important constraints relating to the skull post design include precise positioning of the reference frame relative to the patient's head, relatively long-term fixation, and allowing for movement of the patient's head without deviation of a position of the reference frame relative to the head during the surgical procedure. To satisfy these concerns, available skull post designs incorporate a number of additional screws or pins connected to the main post that are otherwise forced through corresponding holes formed in the skull. Thus, the surgeon is required to make a series of accurately positioned incisions and holes prior to mounting of the skull post. While viable, available skull post designs are therefore highly invasive, and cannot readily accommodate for varying contours of a particular patient's head. Further, the reference frame is typically permanently secured to the skull post such that the entire assembly must be removed following patient registration for subsequent sterilization, and then re-secured to the head. Obviously, any deviation in a position of the skull post (and thus the reference frame) prior to a following sterilization may give rise to localization errors. This same concern will arise with stereotactic procedures performed at other anatomical locations where a bone post is used to affix the reference frame relative to the patient.

Surgical stereotactic systems continue to rapidly evolve with improvements to imaging and display components. However, the currently available skull post (or other bone post) design has essentially remained unchanged, and is unacceptably invasive and may give rise to inaccuracies due to subsequent movement between the reference frame and the patient. Therefore, a need exists for an improved surgical reference frame fixation apparatus.

SUMMARY OF THE INVENTION

One aspect of the present invention provides a surgical fixation device for use in mounting a stereotactic reference frame to a patient. The device includes a mounting bracket assembly, a cannulated post, a base, an anchor tube, a plurality of percutaneous pins, and a driving device. The mounting bracket assembly is adapted to selectively maintain a stereotactic reference frame. The cannulated post defines a top portion, a central portion, a bottom portion and a central passage. The mounting bracket assembly is connected to the top portion. The base is slidably coupled to the bottom portion of the post, and defines a plurality of legs. The anchor tube is connected to the bottom portion of the post, such that the anchor tube extends distally from the post. Respective ones of the percutaneous pins are located to extend distally from respective ones of the legs. Finally, the driving device is connected to the post proximal the base, and is adapted to selectively contact the base. Upon final assembly, the base is longitudinally moveable relative to the anchor tube. With this configuration, the base can be moved to a retracted position such that the anchor tube is readily securable to a bony structure of the patient's anatomy. Once secured, the base can be moved distally such that the percutaneous pins engage the bony structure as well, thereby promoting overall stability of the device relative to the patient. In one preferred embodiment, three of the legs are provided, and are positioned in a tripod-like arrangement. In another preferred embodiment, a retention pin is provided for selectively coupling a bracket of the mounting bracket assembly to the cannulated post such that the bracket will not rotate relative to the post. In yet another preferred embodiment, the device further includes a bone screw used to secure the anchor tube to bone.

Another aspect of the present invention relates to a method of maintaining a stereotactic reference frame relative to a patient's anatomy as part of a stereotactic procedure. The method includes providing a surgical fixation device including a mounting bracket assembly, a cannulated post, a base, an anchor tube, percutaneous pins and a driving device. The post is connected to the mounting bracket assembly. The base is slidably connected to the post. The anchor pin extends distally from the post. The percutaneous pins extend distally from the base. Finally, the driving device is positioned to selectively contact the base. With this construction in mind, the fixation device is articulated to a retracted position in which distal points formed by the percutaneous pins are proximally retracted relative to a distal end of the anchor tube. An incision is formed through skin of the patient to expose a bony structure. The distal end of the anchor tube is inserted through the incision, and secured to the bony structure. For example, in one preferred embodiment, a bone screw is inserted through the cannulated post/anchor tube, and screwed into the bony structure to secure the anchor tube thereto. The percutaneous pins are forced into engagement with the bony structure via movement of the base. Finally, a stereotactic reference frame is mounted to the mounting bracket assembly. In one preferred embodiment, the method further includes registering the patient's anatomy with a stereotactic system employing the reference frame and then removing the reference frame from relative to the patient's anatomy. In this regard, the reference frame is either entirely disassembled from the mounting bracket assembly, or a bracket portion of the mounting bracket assembly remains attached to the reference frame. In either case, the anchor tube remains secured to the bony structure. The reference frame is then sterilized and reassembled to the fixation device.

Yet another aspect of the present invention relates to a method of manufacturing a surgical fixation device otherwise adapted for maintaining a stereotactic reference frame. The method includes providing a cannulated post defining a top portion, a central portion, a bottom portion and a central passage. A driving device is connected to the central portion of the post. A base having a plurality of percutaneous pins extending distally therefrom is slidably connected to the bottom portion of the post. An anchor tube is secured to the bottom portion of the post such that the anchor tube extends distally therefrom. Finally, a mounting bracket assembly is mounted to the top portion of the post. The mounting bracket assembly is adapted to receive a stereotactic reference frame. Upon final assembly, the driving device is positioned to selectively contact the base such that the driving device selectively dictates distal movement of the base relative to the anchor tube. In one preferred embodiment, the driving device is a wing nut threadably secured to the post.

DESCRIPTION OF THE PREFERRED EMBODIMENTS

Figure 1:
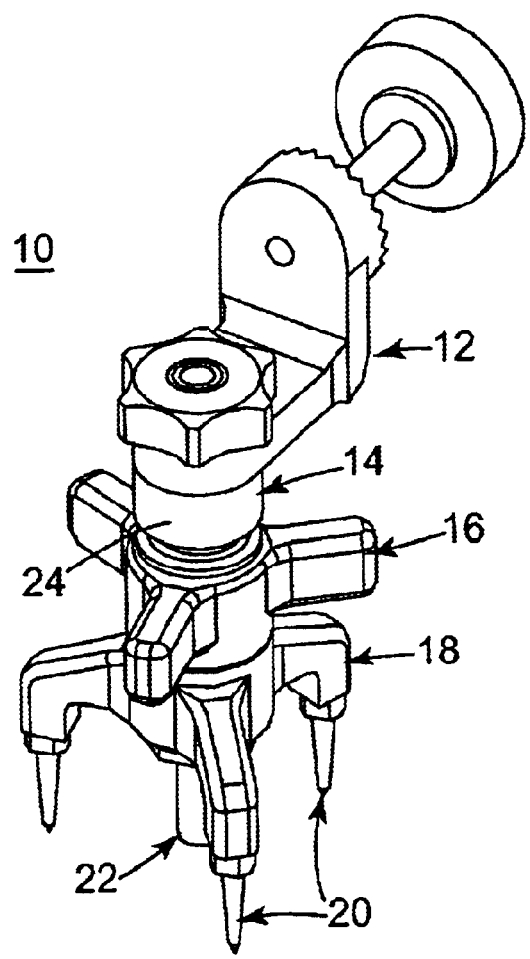
FIG. 1 is a perspective view of a fixation device in accordance with the present invention.

One preferred embodiment of a fixation device 10 in accordance with the present invention is provided in FIG. 1. Although not illustrated, it will be understood that the fixation device 10 is for use with a stereotactic image guidance system (not shown), an example of which is available under the trade name LandMarX® from Medtronic-Xomed, and in particular, for maintaining a reference frame (not shown), such as a dynamic reference frame. With this in mind, the device 10 includes a mounting bracket assembly 12, a cannulated post 14, a wing nut 16, a base 18, a plurality of percutaneous pins 20, and an anchor tube 22. Details on the various components are provided below. In general terms, however, the cannulated post 14 is selectively coupled to the mounting bracket assembly 12. The cannulated post 14 includes a central portion 24 at which the wing nut 16, and below which the base 18 and the anchor tube 22, are secured. More particularly, the anchor tube 22 extends distally from a bottom end of the cannulated post 14. The base 18 is coaxially received over the cannulated post 14 such that the base 18 is slidable relative thereto. The wing nut 16 is coaxially received over the cannulated post 14, between the base 18 and the central portion 24. Finally, the plurality of percutaneous pins 20 extend distally from the base 18. With this configuration, the wing nut 16 can be maneuvered relative to cannulated post 14 to allow and/or force retraction and extension of the base 18, and thus of the percutaneous pins 20, relative to the anchor tube 22.

Figure 2:
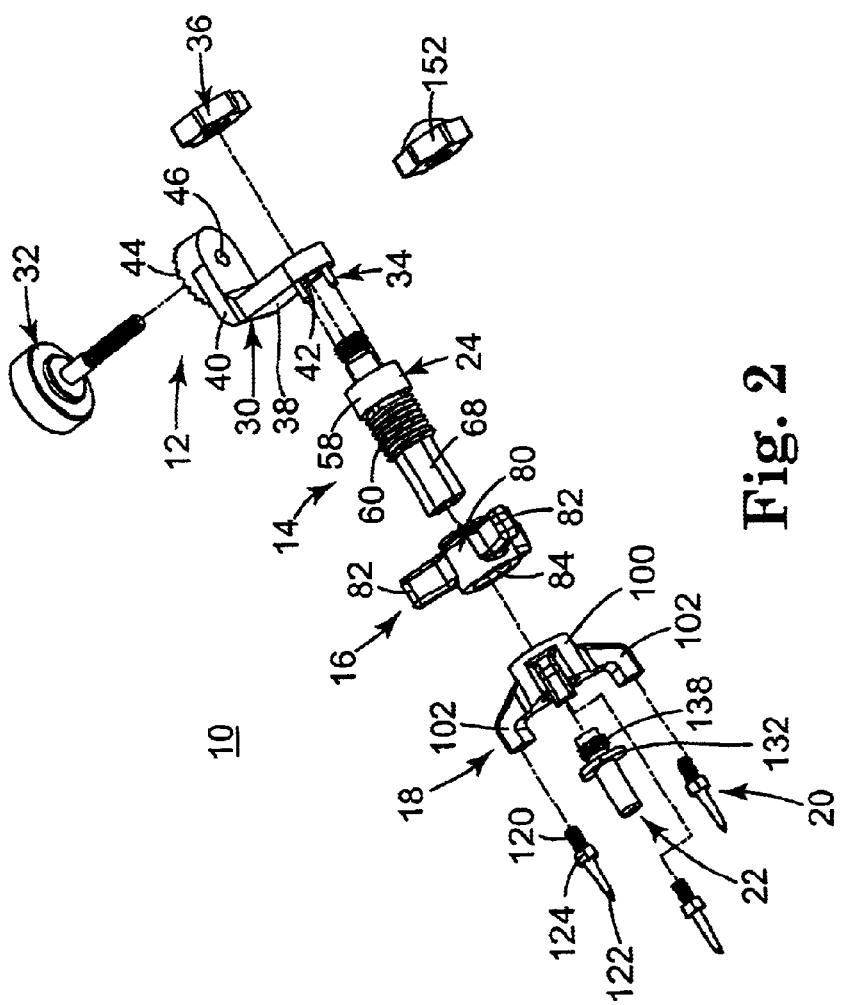
FIG. 2 is an exploded view of the device of FIG. 1.

With additional reference to FIG. 2, the mounting bracket assembly 12 is configured to selectively maintain a reference frame (not shown) and includes a bracket 30, a screw 32, a retention pin 34, and a cannulated nut 36. The bracket 30 is preferably generally L-shaped and includes a horizontal surface 38 and a vertical surface 40. The horizontal surface 38 is configured for abutment with a portion of the cannulated post 14 and forms a bore 42. The horizontal surface 38 further forms a hole (not shown) sized to receive and allow passage of the retention pin 34. As described below, the retention pin 34 is sized for passage through the hole in a horizontal surface 38 as well as through a corresponding opening in the cannulated post 14. The vertical surface 40 is configured for rigid, selective coupling to the reference frame and preferably includes a starburst or toothed portion 44 having a passage 46 formed centrally therethrough. The central passage 46 is threaded to threadably receive the screw 32. In a preferred embodiment, each component of the mounting bracket assembly 12 is formed from a rigid material, preferably stainless steel. Upon final assembly, the retention pin 34 is press fitted to the bracket 30 and serves to rigidly maintain a position of the bracket 30 relative to the cannulated post 14. That is to say, as described in greater detail below, the retention pin 34 assures the exact placement of the reference frame used in patient registration following removal of the reference frame for sterilization, thereby preventing possible registration error. Alternatively, the retention pin 34 can be formed as an extension of the bracket 30. Even further, the retention pin 34 can be eliminated where rotational movement of the bracket 30 relative to the cannulated post 14 is desired upon final assembly.

Figure 3:
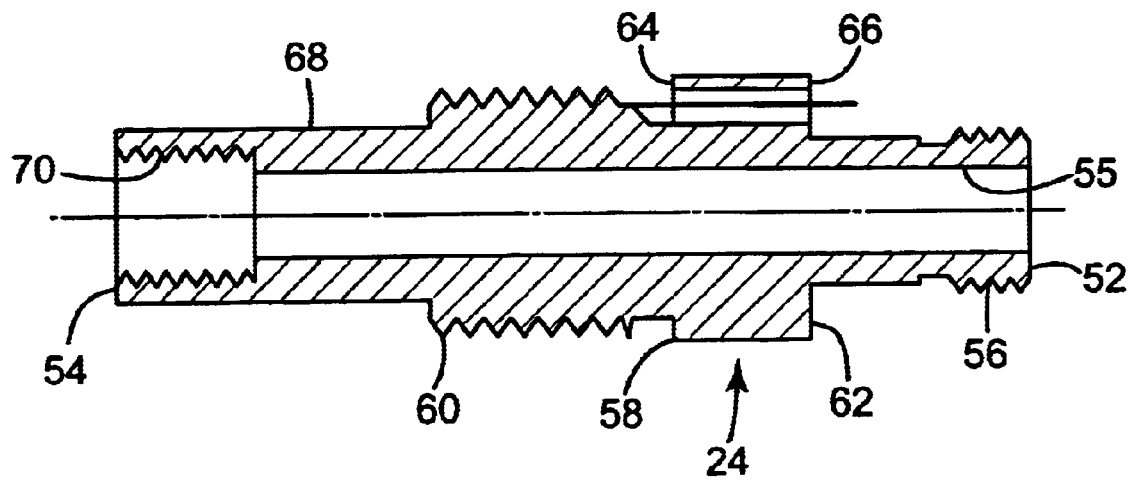
FIG. 3 is a cross-sectional view of a cannulated post portion of the device of FIG. 1.

The cannulated post 14 is an elongated, tubular body formed from a rigid material such as 17-4 stainless steel. With additional reference to FIG. 3, in one preferred embodiment the cannulated post 14 defines a top end or portion 52, the central portion 24, a bottom end or portion 54, and a central passage 55 extending through the cannulated post 14 from the top end 52 to the bottom end 54.

The top end or portion 52 is configured for coupling to the nut 36 of the mounting bracket assembly 12 and includes exterior threads 56. Further, the top end 52 is sized for passage through the bore 42 otherwise associated with horizontal surface 38 of the bracket 30.

The central portion 24 includes a shoulder 58 and exterior threads 60. As shown in the Figures, the shoulder 58 defines a diameter greater than a remainder of the cannulated post 14 and defines an upper stop surface 62 and a lower stop surface 64. Further, a longitudinal bore 66 is preferably formed through the shoulder 58 and is sized to receive the retention pin 34. Conversely, the shoulder 58 can be formed to include a pin extending therefrom (akin to the retention pin 34) that is selectively received by the hole (not shown) in the bracket 30. Regardless, the exterior threads 60 are formed distal the shoulder 58 and are sized to threadably receive a portion of the wing nut 16 as described in greater detail below. A receiving surface 68 is defined distal the exterior thread 60, extending to the bottom end 54. The receiving surface 68 is configured to slidably receive the base 18 and is preferably non-circular, more preferably hexagonal, in transverse cross-section (as best shown in FIG. 2). With this configuration, and as described in greater detail below, a hexagonal or similarly-shaped form of the receiving surface 68 allows for longitudinal sliding of the base 18 relative to the cannulated post 14, but prevents or otherwise impedes rotation of the base 18 about the cannulated post 14. Finally, the central passage 55, otherwise extending through the cannulated post 14, is interiorly threaded 70 at the bottom end 54 to threadably receive the anchor tube 22.

In one preferred embodiment, the cannulated post 14 has an overall length of 1.65 inches, the shoulder 58 has a longitudinal length or thickness of 0.25 inch and a diameter of 0.5 inch. The receiving surface 68 has a longitudinal length (distance between the bottom end 54 and the exterior threads 60) of 0.563 inch. While the receiving surface 68 has been described as preferably being hexagonal in transverse cross-section, other non-circular shapes are equally acceptable (e.g., triangular, square, etc.). Even further, the receiving surface 68 can be circular in transverse cross-section.

Figure 4:
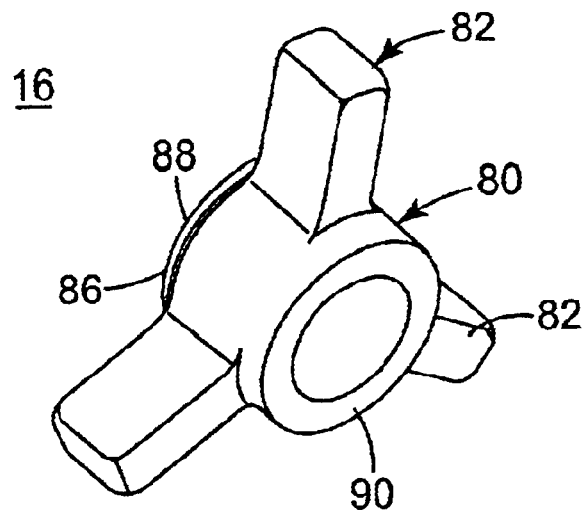
FIG. 4 is an enlarged perspective view of a wing nut portion of the device of FIG. 1.

Returning to FIG. 2, the wing nut 16 is preferably formed from a rigid material such as 17-4 stainless steel, and includes a central body 80 and a plurality of fingers 82 extending radially therefrom. As is known with other wing nut designs, the fingers 82 provide convenient surfaces for grasping by a user, and facilitate placement of a moment force on the wing nut 16. The central body 80 forms an internally threaded passage 84 configured to threadably engage the exterior thread 60 associated with the exterior thread 60 associated with the cannulated post 14. Further, the central body 80 preferably forms a proximal flange 86 forming a proximal abutment surface 88 as best shown in FIG. 4. As described below, the proximal abutment surface 88 is configured to selectively engage the lower stop surface 64 defined by the cannulated post 14. Further, the central body 80 forms a distal abutment surface 90 configured to interface with a portion of the base 18. In a preferred embodiment, the central body 80 has a longitudinal length of 0.437 inch, and the central passage 84 has a diameter of 0.4375 inch. Alternatively, other dimensions are equally acceptable. Even further, the wing nut 16 can be replaced by other driving devices known in the art.

Figure 5:
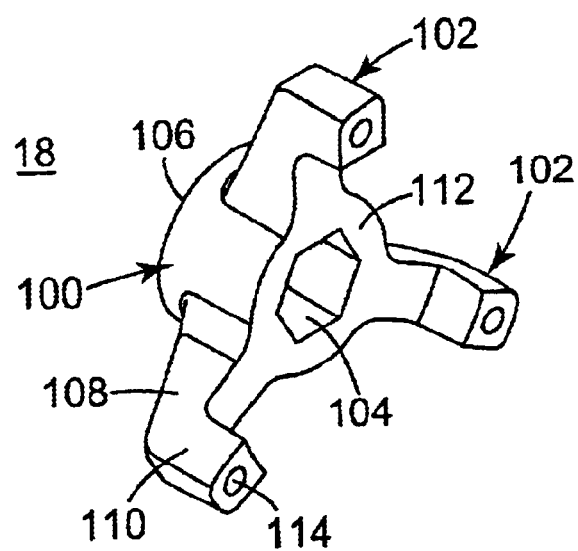
FIG. 5 is an enlarged perspective view of a base portion of the device of FIG. 1.

Returning to FIG. 2, and with additional reference to FIG. 5, the base 18 includes a central body 100 and a plurality of legs 102 extending in a radial fashion therefrom. In a preferred embodiment, three of the legs 102 are provided, and are equidistantly space about a circumference of the central body 100. As a result, and with the preferred embodiment, the base 18 preferably assumes a tripod-like configuration, with each of the legs 102 being positioned 120° from one another. The central body 100 defines an internal bore 104 that is shaped in accordance with a shape of the receiving surface 68 otherwise formed by the cannulated post 14. Thus, in one preferred embodiment where the receiving surface 68 is hexagonal in transverse cross-section, the internal bore 104 similarly assumes a hexagonal shape. By forming the internal bore 104 to a shape corresponding with that of the receiving surface 68, the base 18 can slide in a longitudinal fashion along the receiving surface 68, yet interaction between the receiving surface 68 and the internal bore 104 prevents or impedes rotation of the base 18 about the cannulated post 14. Finally, the central body 100 defines an upper engagement surface 106. As described below, the upper engagement surface 106 is configured to selectively abut the distal abutment surface 90 of the wing nut 16.

Each of the legs 102 includes a radial extension portion 108 and a foot 110. The radial extension portion 108 extends in a generally radial fashion from the central body 100. The foot 110 extends longitudinally (relative to a central axis defined by the internal bore 106), preferably beyond a lower surface 112 otherwise defined by the central body 100. For example, in one preferred embodiment, the foot 110 extends approximately 0.187 inch from the lower surface 112. Further, each of the feet 110 is tapped with a hole 114 sized to receive a respective one of the percutaneous pins 20.

In a preferred embodiment, the base 18 is integrally formed from a rigid material such as 17-4 stainless steel. The central body 100 has an outer diameter of 0.562 inch, with each of the radial extension portions 108 extending to a radius of 0.715 inch relative to the central axis of the central body 100.

Returning to FIG. 2, and as previously described, the percutaneous pins 20 are configured for attachment to a respective one of the legs 102 associated with the base 18. Thus, in the preferred embodiment, three of the percutaneous pins 20 are provided. In one preferred embodiment, each of the percutaneous pins 20 includes a threaded proximal portion 120 and terminates at a distal point 122. The threaded proximal portion 120 is appropriately configured for threadably attachment to a respective one of the legs 102, it being understood that other coupling configurations are equally acceptable. With this in mind, each of the pins 20 further defines a shoulder 124 effectively serving as a stop point relative to engagement with the respective leg 102. With this in mind, and in one preferred embodiment, each of the percutaneous pins 120 are formed such that the distal point 122 extends 0.5 inch from the shoulder 124 so that upon final assembly, the distal point 122 is positioned 0.5 inch from a bottom of the respective foot 110. In a preferred embodiment, the percutaneous pins 120 are formed from a rigid material such as 17-4 stainless steel. By preferably forming the percutaneous pins 120 to be selectively attachable to, and thus removable from, the base 18, in the event one of the percutaneous pins 120 is bent during a surgical procedure, it can easily be replaced.

Figure 6:
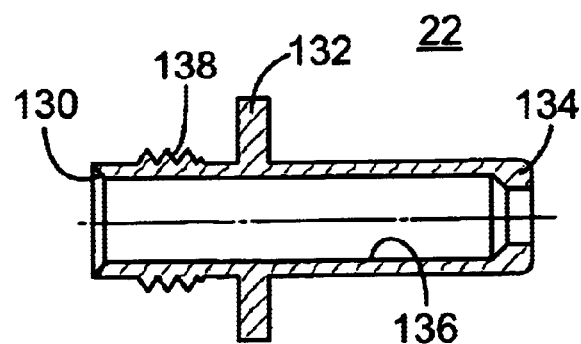
FIG. 6 is a cross-sectional view of an anchor tube portion of the device of FIG. 1.

With additional reference to FIG. 6, the anchor tube 22 is a tubular body preferably forming a proximal end 130, an intermediate flange 132, and distal end 134, and a central passage 136. The passage 136 extends from the proximal end 130 to the distal end 134, and preferably tapers in diameter at the distal end 134. Further, the anchor tube 22 preferably forms exterior threads 138 adjacent the proximal end 130. With this configuration, the anchor tube 22 is formed for threadable engagement with the interior threads 70 otherwise formed by the cannulated post 14. Further, the intermediate flange 132 is sized to abut the lower surface 112 otherwise provided by the central body 100 of the base 18. With this configuration, and upon final assembly, then, the flange 132 dictates a defined extension of the anchor tube 22, and in particular the distal end 134, relative to the base 18. Alternatively, the flange 132 can be eliminated.

The fixation device 10 is assembled in accordance with one preferred embodiment substantially as follows. The wing nut 16 is coaxially received over the cannulated post 14, and threaded to the exterior thread 60. The percutaneous pins 20 are assembled to respective ones of the legs 102 formed by the base 18. The base 18 is then coaxially received over the receiving surface 68 of the cannulated post 14 via the internal bore 104. The anchor tube 22 is then secured to the bottom end 54 of the cannulated post 14 via threadable engagement between the exterior threads 138 and the interior thread 70. Finally, the mounting bracket assembly 12 is assembled to the top end 52 of the cannulated post 14 as previously described.

The above-described preferred assembly allows the wing nut 16 to be rotated about the cannulated post 14 via threadable engagement provided at the exterior threads 60. Further, the distal abutment surface 90 of the wing nut 16 interfaces with the upper engagement surface 106 of the base 18. Thus, by rotating the wing nut 16 relative to the cannulated post 14, the wing nut 16 allows for retraction and extension of the base 18 relative to the cannulated post 14 and thus the anchor tube 22. In this regard, a maximum retraction level is defined by abutment between the proximal abutment surface 88 of the wing nut 16 and the lower stop surface 64 of the cannulated post 14. As best shown in FIG. 1, when the base 18 is fully retracted, the anchor tube 22, and in particular the distal end 134, extends distally beyond the percutaneous pins 20 otherwise secured to the base 18. Subsequent rotation of the wing nuts 16 forces the base 18 to extend or move/slide distally relative to the anchor tube 22 such that the distal points 122 approach a level of the distal end 134 of the anchor tube 22 (i.e., the distal points 122 are less proximally retracted relative to the distal end 134).

Although not shown, to best effectuate forced movement of the base 18 via the wing nut 16 during a surgical procedure, the fixation device 10 preferably further includes a bone screw (not shown) that is sized for insertion through the post cannulated post 14 and the anchor tube 22. With this preferred embodiment, a head portion of the bone screw nests within the distal end 134 of the anchor tube 22 whereas a threaded portion extends distally therefrom and is secured to the patient's bony structure (not shown). This direct connection between the anchor tube 22 and the bony structure effectively "locks" the anchor tube 22 to the bony structure, so that as the base 18 is forced distally via movement of the wing nut 16, the bony structure supports and stabilizes the anchor tube 22, and thus the fixation device 10, against the torque generated during rotation of the wing nut 16.

During use, the fixation device 10 is placed in the retracted position of FIG. 1. The surgeon (not shown) then determines the appropriate application site for the fixation device 10. The fixation device 10 is generally applied transcutaneously through a small incision, however, it can be applied directly to the anatomical bone structure if larger surgical incisions are planned. For example, skull-base surgery application sites include the temporal, occipital, parietal, and frontal bones. A convenient site for endoscopic sinus surgery is the parietal bone of the non-dominant hemisphere. Further, the fixation device 10 can be applied at a wide variety of other anatomical locations as part of a stereotactic procedure at that location. In other words, the fixation device 10 can be mounted to any bony structure such as vertebrae, pelvis, other large bones, etc.

With reference to one preferred method in which the fixation device 10 is applied to the patient's cranium, once the desired application site is determined, a small scalp incision (on the order to 10 mm) is made. The incision is preferably carried through the galea aponeurosis and the pericranium. Preferably, a 7 mm diameter area of parietal bone should be exposed with a periosteal elevator.

Figure 7:
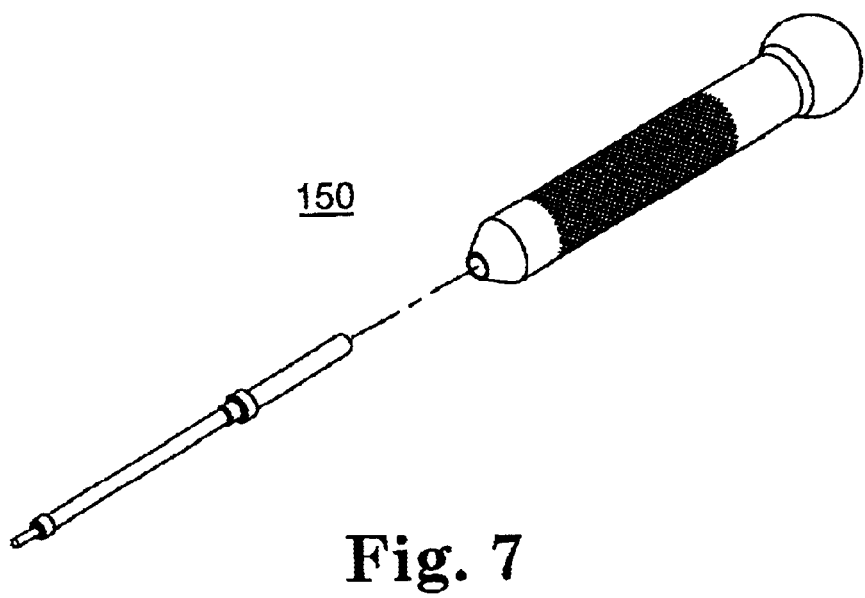
FIG. 7 is a perspective view of a drill useful with the device of FIG. 1.

The distal end 134 of the anchor tube 22 is then inserted through the incision, perpendicular to the calvarium. Because the base 18, and thus the percutaneous pins 20, is fully retracted relative to the anchor tube 22, a surgeon is able to easily confirm that the anchor tube 22 is flush against the skull. Pressure is applied to the device 10 until the anchor tube 22 is flush with the cranium (or other bony structure), causing the percutaneous pins 20 to pierce the skin. A hand drill, such as the hand drill 150 of FIG. 7, is inserted through the cannulated post 14 and the anchor tube 22, and used to create a pilot hole in the bony structure. In this regard, the fixation device 10 is configured to serve as a guide for the hand drill 150. Further, the hand drill 150 preferably forms a shoulder along a length of a shaft thereof, sized to contact the cannulated post 14 and thereby serve as a depth stop to further distal movement of the drill 150. A length of the drill 150 distal the shoulder corresponds with a thread length of a bone screw (not shown) otherwise used to secure the anchor tube 22 to the bony structure as described below.

Figure 8:
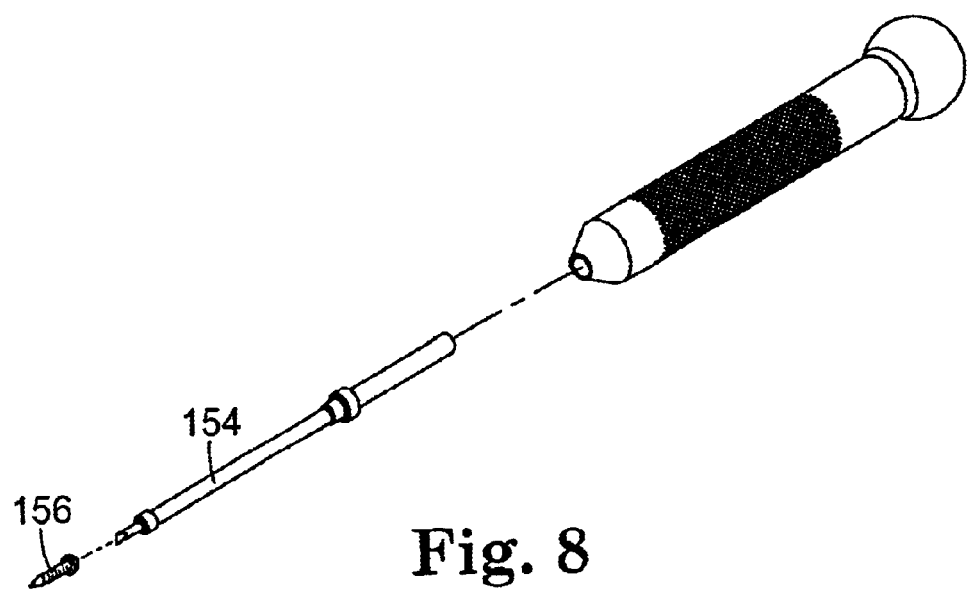
FIG. 8 is a perspective view of a screwdriver and bone screw useful with the device of FIG. 1.

The drill 150 is then removed. With further reference to FIG. 8, a screwdriver 154 maintaining a bone screw 156 is then inserted into the pilot hold via the passage 136 of the anchor tube 22. The bone screw 156 is seated into the bony structure, and locks against the anchor tube 22 (such as at the tapered inner surface shown in FIG. 6). In one preferred embodiment, the screwdriver 154 has a shoulder similar to that of the hand drill 150 (FIG. 7), again for ensuring that the bone screw 156 is not forced beyond an acceptable depth in the bony structure. In one preferred embodiment, the bone screw 156 has a thread length (from a head of the bone screw 156) of 5 mm, although other dimensions are acceptable.

The wing nut 16 is then rotated to force the base 18 toward the distal end 134 of the anchor tube 22. In particular, the percutaneous pins 20 are forced into engagement with the bony structure with movement of wing nut 16. The bone screw 156 maintains a position of the fixation device 10, offsetting any torque forces generated by movement of the wing nut 16, via rigid coupling of the anchor tube 22 to the bony structure. That is to say, interaction between the receiving surface 68 of the cannulated post 14 and the internal bore 104 of the base 18 prevents the base 18 from twisting or otherwise turning relative to the cannulated post 14 as the wing nut 16 is rotated to force the base 18, and thus the percutaneous pins 20, downwardly. In a preferred embodiment, the flange 132 otherwise associated with the anchor tube 22 serves as a stop to limit the depth of insertion of both the anchor tube 22 and the percutaneous pins 20. Finally, a cap 152 (FIG. 1) is preferably secured over the nut 36 (FIG. 1), thereby closing the central passage 55 (FIG. 2) of the cannulated post 14 to maintain a sterile field. The reference frame (not shown) can then be mounted to the fixation device 10.

In accordance with an alternative method of use in accordance with the present invention, the anchor tube 22 is secured to the bony structure by the user placing a downward force on the device 10 following insertion of the anchor tube 22 through the incision. Though less preferred, this technique can provide sufficient support between the anchor tube 22 and the bony structure without requiring a bone screw.

In addition to providing a minimally invasive application procedure, as well as a laterally stable attachment (via the tripod configuration of the base 18 and thus of the percutaneous pin 20), the fixation device 10 allows for convenient, accurate removal and reattachment of a reference frame (not shown) via the mounting bracket assembly 12. In particular, the reference frame is secured to the bracket 30 via the screw 32 and the starburst teeth 44. During a typical procedure, the entire assembly, including the fixation device 10 and the reference frame, is secured to the patient's skull (or other anatomical location) and the patient's relevant anatomy is "registered" in a non-sterile environment. Subsequently, it may be necessary to remove the reference frame for sterilization. In this regard, by coupling the bracket 30 to the shoulder 58 of the cannulated post 14 via the retention pin 34, a position of the bracket 30 relative to the cannulated post 14 will not change. Thus, the retention frame can be removed from the mounting bracket assembly 12, sterilized, and then re-secured thereto. Alternatively, the nut 36 can be unthreaded, and the bracket 30/reference frame can be removed, sterilized as a unit, and the bracket 30 (and thus the reference frame) re-secured to the cannulated post 14. With either technique, the bracket 30 is positioned at precisely the same position relative to the cannulated post 14 via the retention pin 34, and thus the reference frame will be in the exact same position utilized during the registration following sterilization and re-assembly.

The fixation device of the present invention provides a marked improvement over previous skull or bone post designs. In particular, the fixation frame provides a minimally invasive technique to fixate a reference frame to the cranium or other anatomical location in a rigid and rapid manner, that also allows for movement of the patient's head (or other relevant anatomy) during surgical procedures. In particular, an anchor tube initially secures the device to the head or other bony structure. Configuration of, and interaction between, the cannulated post, the wing nut and the base allows the preferably triangularly arranged percutaneous pins to be readily inserted through the patient's skin, thereby ensuring lateral stability and sustaining localization accuracy during surgical navigation. Finally, the mounting bracket assembly allows for removal and sterilization of a reference frame, and subsequent reattachment at a precise location and orientation.

Although the present invention has been described with reference to preferred embodiments, workers skilled in the art will recognize that changes can be made in form and detail without departing from the spirit and scope of the present invention. For example, preferred dimensional characteristics have been ascribed for each of the various components. It will be understood, however, that a wide variety of other dimensions, either greater or smaller, are equally acceptable. Further, the preferred method of use of the fixation device has been described with reference to a patient's skull. Alternatively, the fixation device can be applied in a similar manner to a variety of other anatomical locations, such as the vertebrae, pelvis, other large bones, etc. Further, the fixation device can be made available as a kit, including the fixation device, a hand drill, a screwdriver and one or more bone screws as previously described.

What is claimed is:

1. A surgical fixation device for use in mounting a stereotactic reference frame to a patient, the device comprising:
    a mounting bracket assembly adapted to selectively maintain a stereotactic reference frame;
    a cannulated post defining a top portion, a central portion, a bottom portion, and a central passage, the top portion being connected to the mounting bracket assembly;
    a base slidably coupled to the bottom portion of the post, the base defining a plurality of legs;
    an anchor tube connected to, and extending distally from, the bottom portion of the post;
    a plurality of percutaneous pins respective ones of which extend distally from respective ones of the legs; and
    a driving device connected to the post proximal the base, the driving device adapted to selectively contact the base;
    wherein upon final assembly, the base is longitudinally moveable relative to the anchor tube.

2. The device of claim 1, wherein the anchor tube terminates in a distal end opposite the post and each of the percutaneous pins forms a distal point extending opposite the base, and further wherein the device is adapted such that the base is longitudinally movable between a retracted position in which the distal points are proximally retracted relative to the distal end and an extended position in which the distal points are less proximally displaced relative to the distal end.

3. The device of claim 2, wherein the device is adapted such that in the extended position, the distal points are substantially level with the distal end.

4. The device of claim 1, wherein the mounting bracket assembly includes a bracket and a nut, the nut being threadably connected to the top portion of the post to couple the bracket to the post.

5. The device of claim 4, wherein the mounting bracket assembly further includes a retention pin selectively connecting the bracket to a portion of the post so as to selectively prevent rotation of the bracket relative to the post.

6. The device of claim 1, wherein the central portion of the post includes a shoulder defining a lower stop surface for selectively contacting the driving device.

7. The device of claim 6, wherein the shoulder further defines an upper stop surface for selectively contacting a portion of the mounting bracket assembly.

8. The device of claim 6, wherein the central portion further includes a threaded surface distal the shoulder.

9. The device of claim 8, wherein the threaded surface is adapted to threadably engage the driving device.

10. The device of claim 1, wherein the bottom portion of the post defines an outer surface adapted for slidably receiving the base.

11. The device of claim 10, wherein the outer surface is hexagonal in transverse cross-section.

12. The device of claim 1, wherein the bottom portion of the post defines an interior threaded surface adapted to threadably engage the anchor tube.

13. The device of claim 1, wherein the base includes three legs.

14. The device of claim 13, wherein the three legs are equidistantly spaced.

15. The device of claim 1, wherein each of the legs includes a foot adapted to receive a respective one of the pins.

16. The device of claim 1, wherein the base further includes a central body from which the plurality of legs extend, the central body defining an internal bore having a transverse cross-sectional shape corresponding with a transverse cross-sectional shape of the bottom portion of the post.

17. The device of claim 16, wherein the transverse cross-sectional shape is non-circular.

18. The device of claim 16, wherein the central body defines an upper engagement surface adapted to selectively contact a portion of the driving device.

19. The device of claim 1, wherein three of the percutaneous pins are provided.

20. The device of claim 1, wherein the driving device is a wing nut.

21. The device of claim 1, wherein the driving device is rotatably secured to the post proximal the base.

22. The device of claim 21, wherein the driving device is threadably secured to the post and defines a distal abutment surface, and further wherein distal movement of the driving device relative to the post causes the distal abutment surface to apply a force onto the base.

23. The device of claim 1, wherein the anchor tube includes a proximal end adapted for connection to the bottom portion of the post.

24. The device of claim 23, wherein the anchor tube further includes an intermediate flange adapted to selectively contact the base.

25. The device of claim 23, wherein the anchor tube further includes a distal end and a central passage, the central passage of the anchor tube having a reduced diameter at the distal end thereof.

26. A method of maintaining a reference frame relative to a patient's anatomy as part of a surgical stereotactic procedure, the method comprising:
   providing a surgical fixation device including a mounting bracket assembly, a cannulated post connected to the mounting bracket assembly, a base slidably connected to the post, an anchor tube extending distally from the post, percutaneous pins extending distally from the base, and a driving device for selectively contacting the base;
   articulating the surgical fixation device to a retracted position in which distal points formed by the percutaneous pins are proximally retracted relative to a distal end of the anchor tube;
   forming an incision through skin of the patient to expose a bony structure;
   inserting the distal end of the anchor tube through the incision;
   securing the distal end of the anchor tube to the bony structure;
   forcing the percutaneous pins into engagement with the bony structure via movement of the base; and
   mounting a stereotactic reference frame to the mounting bracket assembly.

27. The method of claim 26, wherein the base includes three legs each maintaining a distally extending percutaneous pin, and further wherein forcing the percutaneous pins into engagement with the bony structure includes driving three of the percutaneous pins into the bony structure.

28. The method of claim 27, wherein the three percutaneous pins are equidistantly spaced relative to a circumference of the anchor tube.

29. The method of claim 26, wherein forcing the percutaneous pins into engagement with the bony structure includes manipulating the driving device to impart a distal movement onto the base.

30. The method of claim 29, wherein the driving device includes a wing nut threadably secured to the post proximal the base, and further wherein manipulating the driving device includes rotating the wing nut about the post such that the wing nut moves distally into contact with the base.

31. The method of claim 26, wherein the base is slidable relative to the anchor tube such that forcing the percutaneous pins into engagement with the bony structure includes sliding the base relative to the anchor tube.

32. The method of claim 26, further comprising:
   piercing the skin with the percutaneous pins prior to securing the distal end of the anchor tube to the bony structure.

33. The method of claim 26, wherein securing the distal end of the anchor tube to the bony structure includes coupling the distal end to the bony structure with a bone screw.

34. The method of claim 33, wherein the anchor tube includes a central passage, and further wherein coupling the distal end to the bony structure with a bone screw includes locating a portion of the bone screw within the central passage of the anchor tube.

35. The method of claim 34, further comprising:
   creating a pilot hole in the bony structure below the distal end of the anchor tube prior to inserting the bone screw.

36. The method of claim 35, wherein creating a pilot hole includes guiding a hand drill through aligned, central passages of the post and the anchor tube.

37. The method of claim 26, wherein forcing the percutaneous pins into engagement with the bony structure includes stabilizing the fixation device relative to the bony structure.

38. The method of claim 26, further comprising:
   a. registering the patient's anatomy with a stereotactic system after mounting the reference frame to the mounting bracket assembly;
   b. removing the reference frame relative to the patient's anatomy, wherein the anchor tube remains secured to the bony structure;
   c. sterilizing the reference frame; and
   d. re-mounting the reference frame to the mounting bracket assembly.

39. The method of claim 38, wherein removing the reference frame includes disassembling the reference frame from the mounting bracket assembly.

40. The method of claim 38, wherein the mounting bracket assembly includes a bracket adapted to receive the reference frame and a retention device for coupling the bracket to the post, and further wherein removing the reference frame includes manipulating the retention device to release the bracket from the post.

41. The method of claim 26, wherein the bony structure is a cranium.

42. The method of claim 26, wherein the bony structure is a vertebra.

43. The method of claim 26, wherein the bony structure is a pelvic bone.

44. A method of manufacturing a surgical fixation device adapted for maintaining a stereotactic reference frame, the method comprising:
   providing a cannulated post defining a top portion, a central portion, a bottom portion and a central passage;
   connecting a driving device to the central portion of the post;
   slidably connecting a base to the bottom portion of the post, the base having a plurality of percutaneous pins extending distally therefrom;
   securing an anchor tube to the bottom portion of the post such that the anchor tube extends distally therefrom; and
   mounting a mounting bracket assembly to the top portion of the post, the mounting bracket assembly adapted to receive a stereotactic reference frame;
   wherein upon final assembly, the driving device is positioned to selectively contact the base such that the driving device selectively dictates distal sliding movement of the base relative to the anchor tube.

45. The method of claim 44, wherein upon final assembly, the base is slidable between a retracted position in which distal points formed by the percutaneous pins are proximally retracted relative to a distal end of the anchor tube and an extended position in which the distal point are less proximally retracted relative to the distal end of the anchor tube.

46. The method of claim 44, wherein the driving device includes a wing nut, and further wherein connecting the driving device to the post includes threading the wing nut to threads formed on the central portion of the post.

47. The method of claim 46, wherein the central portion further includes a shoulder proximal the threads, the shoulder defining an outer dimension greater than an inner diameter of the wing nut, and further wherein connecting the driving device to the post further includes:
   a. co-axially sliding the wing nut over the bottom portion of the post;
   b. threadably connecting the wing nut to the threads; and
   c. rotating the wing nut along the threads such that the wing nut is proximate the shoulder prior to slidably connecting the base to the post.

48. The method of claim 44, wherein the bottom portion of the post and a central body of the base define corresponding receiving surfaces that are non-circular in transverse cross-section, and further wherein slidably connecting the base to the post includes aligning the receiving surface of the base with the receiving surface of the post.

49. The method of claim 44, wherein the base forms a plurality of legs, the method further comprising:
   securing respective ones of the percutaneous pins to respective ones of the legs.

50. The method of claim 49, wherein each of the percutaneous pins are threadably secured to the respective legs.

51. The method of claim 49, wherein upon final assembly, the anchor tube is centrally positioned relative to the legs.

52. The method of claim 44, wherein the anchor tube is threadably secured to the post.

53. The method of claim 44, wherein the anchor tube forms a passage, and further wherein upon final assembly, the passage of the anchor tube is aligned with the central passage of the post.

54. The method of claim 44, wherein the mounting bracket assembly includes a bracket forming a bore and a nut, and further wherein mounting the mounting bracket assembly includes:
   placing the bore over the top portion of the post; and
   threadably securing the nut to the top portion such that the nut retains the bracket relative to the post.

55. The method of claim 44, wherein the mounting bracket assembly includes a bracket and a retention pin, and further wherein mounting the mounting bracket assembly includes:
   connecting the retention pin to the bracket and the post such that the retention pin prevents rotation of the bracket relative to the post.

* * * * *